(12) United States Patent
Imhof

(10) Patent No.: US 8,801,797 B2
(45) Date of Patent: Aug. 12, 2014

(54) JOINT SOCKET FOR A HIP ENDOPROSTHESIS

(75) Inventor: Martin Imhof, Meggen (CH)

(73) Assignee: Smith and Nephew Orthopaedics AG, Rotkreuz (CH)

( * ) Notice: Subject to any disclaimer, the term of this patent is extended or adjusted under 35 U.S.C. 154(b) by 2047 days.

(21) Appl. No.: 10/596,752

(22) PCT Filed: Dec. 13, 2004

(86) PCT No.: PCT/EP2004/014151
§ 371 (c)(1), (2), (4) Date: Dec. 8, 2008

(87) PCT Pub. No.: WO2005/063148
PCT Pub. Date: Jul. 14, 2005

(65) Prior Publication Data
US 2009/0171464 A1    Jul. 2, 2009

(30) Foreign Application Priority Data
Dec. 22, 2003 (DE) ................... 103 60 390

(51) Int. Cl.
*A61F 2/34* (2006.01)
(52) U.S. Cl.
USPC .................. 623/22.24; 623/22.28; 623/22.25
(58) Field of Classification Search
USPC .......... 623/22.11, 22.15–22.21, 22.23–22.29, 623/22.31–22.32, 22.38, 22.4, 23.12
See application file for complete search history.

(56) References Cited

U.S. PATENT DOCUMENTS

| | | | |
|---|---|---|---|
| 4,894,064 A * | 1/1990 | Imhof | 623/22.31 |
| 5,725,589 A | 3/1998 | Pfaff | |
| 5,879,397 A | 3/1999 | Kalberer | |
| 2002/0068980 A1 * | 6/2002 | Serbousek et al. | 623/22.29 |
| 2002/0147499 A1 | 10/2002 | Shea et al. | |

FOREIGN PATENT DOCUMENTS

| | | |
|---|---|---|
| DE | 43 35 931 A1 | 4/1995 |
| DE | 44 28 290 A1 | 2/1996 |
| EP | 0 655 230 A | 5/1995 |
| EP | 0 663 193 | 7/1995 |
| EP | 0 694 294 A | 1/1996 |

OTHER PUBLICATIONS

International Search Report for PCT Application No. PCT/EP2004/014151, mailed Apr. 4, 2005.
International Preliminary Report-PCT-EP2004014151, filed Dec. 13, 2004, in 5 pages.

* cited by examiner

*Primary Examiner* — Marcia Hoffman
(74) *Attorney, Agent, or Firm* — Krieg DeVault LLP

(57) ABSTRACT

A joint socket of a hip endoprosthesis includes a socket shell implantable in the pelvic bone and a socket insert for providing a bearing for the joint head. The socket shell has an accommodating space having a conical inner surface in which the spherical outer surface of the socket insert is inserted. As a result, the socket insert can be clamped in a self-locking manner in any desired position of rotation and tilt in the accommodating space of the socket shell.

30 Claims, 2 Drawing Sheets

JOINT SOCKET FOR A HIP ENDOPROSTHESIS

CROSS-REFERENCE TO RELATED APPLICATIONS

This Application is a US National Phase of the International Application No. PCT/EP2004/0141151 filed Dec. 13, 2004 designating the U.S. and published in German on Jul. 14, 2005 as WO 2005/063148, which claims priority of German Patent Application No. 103 60 390.5, filed Dec. 22, 2003.

BACKGROUND OF THE INVENTION

1. Field of the Invention

The invention relates to a joint socket for a hip endoprosthesis.

2. Description of the Related Art

In the case of total hip endoprostheses, a prosthesis stem having a joint head is inserted into the femur. A joint socket, which serves as a bearing shell for the joint head, is implanted in the pelvic bone. It is known to construct the joint socket from a socket shell and a socket insert. The socket shell can be optimised with regard to implantation in the pelvic bone, whereas the socket insert can be optimised with regard to the bearing properties for the joint head. In that case the socket shell is so formed and so positioned in the pelvic bone as to allow ingrowth that is as stable as possible by the socket shell in the pelvic bone. The socket insert can be oriented in the socket shell in such a way that the joint head is accommodated so that the prosthesis stem and accordingly the femur of the patient are as far as possible in the correct orthopaedic position.

From EP 0 663 193 A1 there is known a joint socket wherein the socket insert has a spherical outer surface and that spherical outer surface is seated in a spherical accommodating space—of the same spherical radius—of the socket shell. Therefore, when the socket insert has been inserted into the socket shell, the socket insert can be rotated at will about its axis of rotation and its axis of rotation can be tilted at will with respect to the axis of rotation of the accommodating space. As a result, it is possible for the socket shell to be positioned in the pelvic bone in accordance with the bone structure. The socket insert can be oriented in accordance with the orthopaedic position of the prosthesis stem inserted into the femur. In order to fix the socket insert in its position within the socket shell, the inner spherical surface of the accommodating space of the socket shell has pointed projecting teeth which engage in the outer surface of the socket insert. Because the teeth have to dig into the outer surface of the socket insert, there are limitations with respect to the choice of material for the socket insert. Pressing the socket insert onto the teeth of the socket shell makes it difficult for the socket insert to be inserted in a precisely positioned manner.

SUMMARY OF THE INVENTION

The problem underlying the invention is to provide a joint socket for a hip endoprosthesis which allows the socket insert to be freely oriented in relation to the socket shell with high precision.

In accordance with one embodiment, a joint socket for a hip endoprosthesis is provided. The joint socket includes a socket shell that is implantable in the pelvic bone and a socket insert for providing a bearing for the joint head of a prosthesis stem. The socket insert has a spherical outer surface configured to sit in an accommodating space defined by the socket shell, such that said outer surface contacts an inner surface of the accommodating space along a line of contact that is concentric with respect to the axis of rotation of the accommodating space. The inner surface of the socket shell, which defines the accommodating space, narrows toward the pole of the accommodating space in such a manner that the radius of curvature in the region of contact between the socket insert and socket shell is always greater than a spherical radius of the outer surface of the socket insert. The socket insert is arranged so as to be clamped in a self-locking manner in the accommodating space.

In accordance with one embodiment, the joint socket for a hip endoprosthesis has a socket shell and a socket insert which, by virtue of its spherical outer surface, allows free rotation and tilting in the socket shell. The socket shell can therefore be implanted in accordance with the anatomy and structure of the pelvic bone, so that optimum conditions for ingrowth can be achieved. The socket insert can be so rotated in the socket shell and its axis of rotation can be so tilted in relation to the axis of rotation of the socket shell that the axis of rotation of the socket insert is aligned with the axis of the shaft neck of the prosthesis stem when the femur with the inserted prosthesis stem is arranged in the optimum orthopaedic position. The spherical outer surface of the socket insert is in contact with the inner surface of the accommodating space along a circumferential line which is concentrically arranged with respect to the axis of rotation of the accommodating space. That line contact makes it possible for the socket insert to be readily rotated and tilted in the accommodating space so that the socket insert can be optimally oriented in terms of its position. Once the socket insert has been oriented, slight pressure is sufficient to press the socket insert into the narrowing accommodating space, whereupon the socket insert becomes clamped in the accommodating space in self-retaining manner. The self-retaining or self-locking clamping force brings about fixing of the socket insert in the socket shell with a high degree of stability; loading of the joint causes additional pressing of the socket insert into the socket shell so that fixing of the socket shell is additionally strengthened.

Because fixing of the optimally oriented socket insert results from its being simply pressed into the accommodating space, this fixing is simple to carry out and does not require any additional instruments or additional fixing means. The self-retaining clamping is established with a minimal amount of displacement of the socket insert into the accommodating space so that unintentional misalignment of the socket insert orientation cannot occur in the course of fixing the socket insert in position.

In the case of an implanted prosthesis, the shank neck of the prosthesis stem can, in unfavourable cases, make contact with the edge of the joint socket (so-called impingement). As a result thereof, the prosthesis stem exerts leverage on the joint socket. In the case of customary joint sockets, in which the socket insert is held in the socket shell with an interlocking fit, that leverage can result in the entire joint socket's being levered out from the pelvic bone or at least becoming loose in the pelvic bone. In accordance with one embodiment of the invention, the socket insert is merely pressed into the accommodating space of the socket shell, so that leverage in an unfavourable case, as discussed above, merely causes loosening of the socket insert in the socket shell. When the joint is subsequently subjected to normal loading, the socket insert is pressed back into the accommodating space of the socket shell and is again firmly clamped and fixed.

In a preferred embodiment, the inner surface of the accommodating space of the socket shell is, at least in the region of the line of contact, in the form of a cone that narrows towards the pole of the accommodating space. As a result thereof, simple manufacture is possible. The conical surface additionally ensures especially effective self-retaining. As the cone angle, that is to say the angle between the mid-axis of the cone and the line of the lateral surface of the cone, there is selected the self-retaining angle corresponding to the material pairing of socket shell and socket insert. Usually, that cone angle is, depending on the material pairing, about from 4° to 10°.

In order to bring about reliable clamping of the socket insert in the socket shell, the socket insert and the socket shell are made from a hard material. The socket shell is preferably manufactured from a biocompatible material, for example a titanium alloy. For the socket insert there can be selected a material corresponding to the sliding characteristics pairing of socket shell and joint head, for example a metallic or ceramic material or a plastics material.

BRIEF DESCRIPTION OF THE DRAWINGS

These and other features, aspects and advantages of the present invention will now be described in connection with the preferred embodiments of the invention, in reference to the accompanying drawings. The illustrated embodiments, however, are merely examples and are not intended to limit the invention. The drawings include the following 2 figures.

DETAILED DESCRIPTION OF THE PREFERRED EMBODIMENTS

Figure 1:
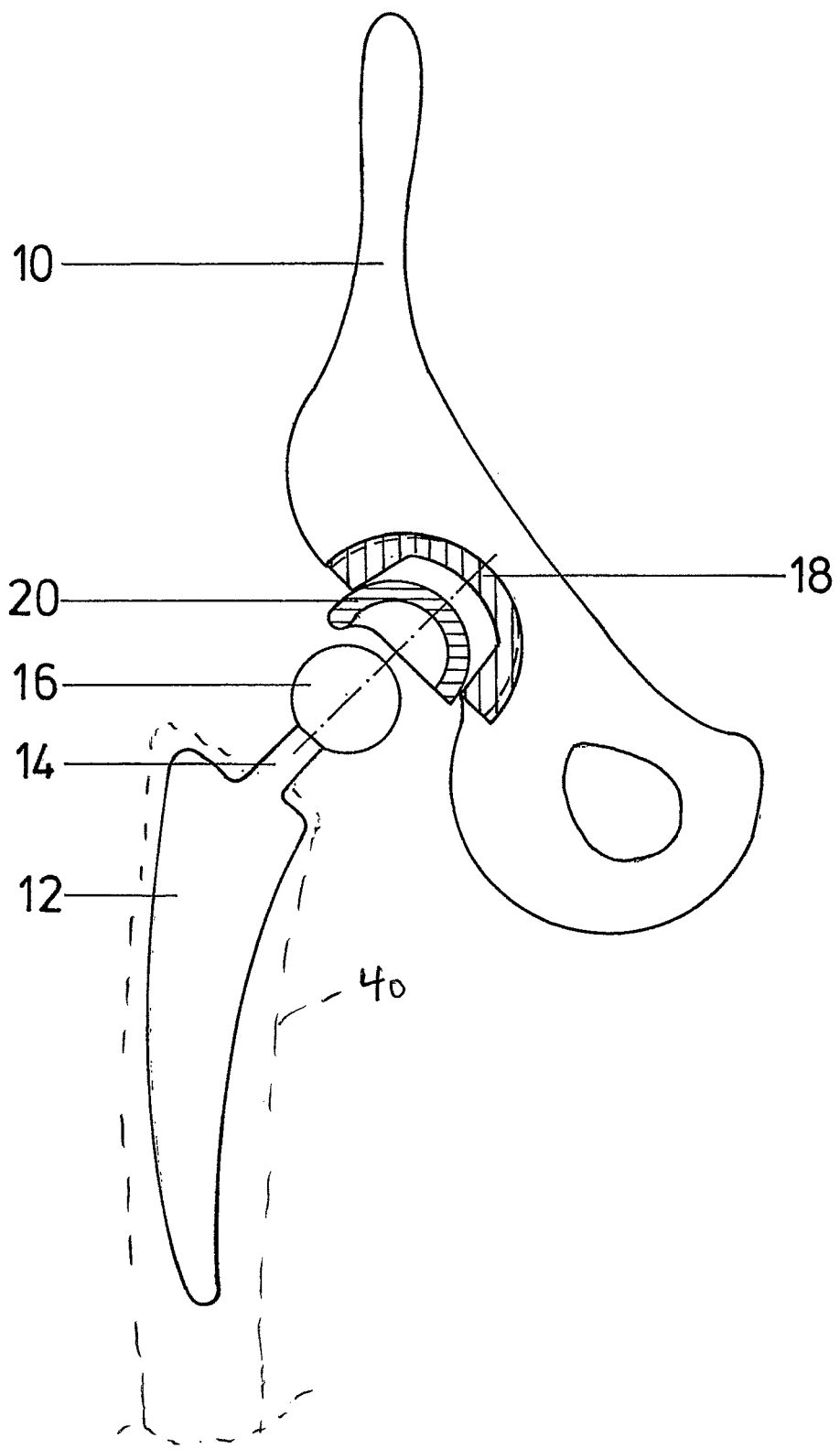
FIG. 1 is a schematic view of one embodiment of a total hip endoprosthesis.

The total hip endoprosthesis consists of a joint socket, which is implantable in the pelvic bone 10, and a prosthesis stem 12, which is inserted into the femur 40. The prosthesis stem 12 has a shaft neck 14, on which a joint head 16 sits, which will be held in the joint socket.

Figure 2:
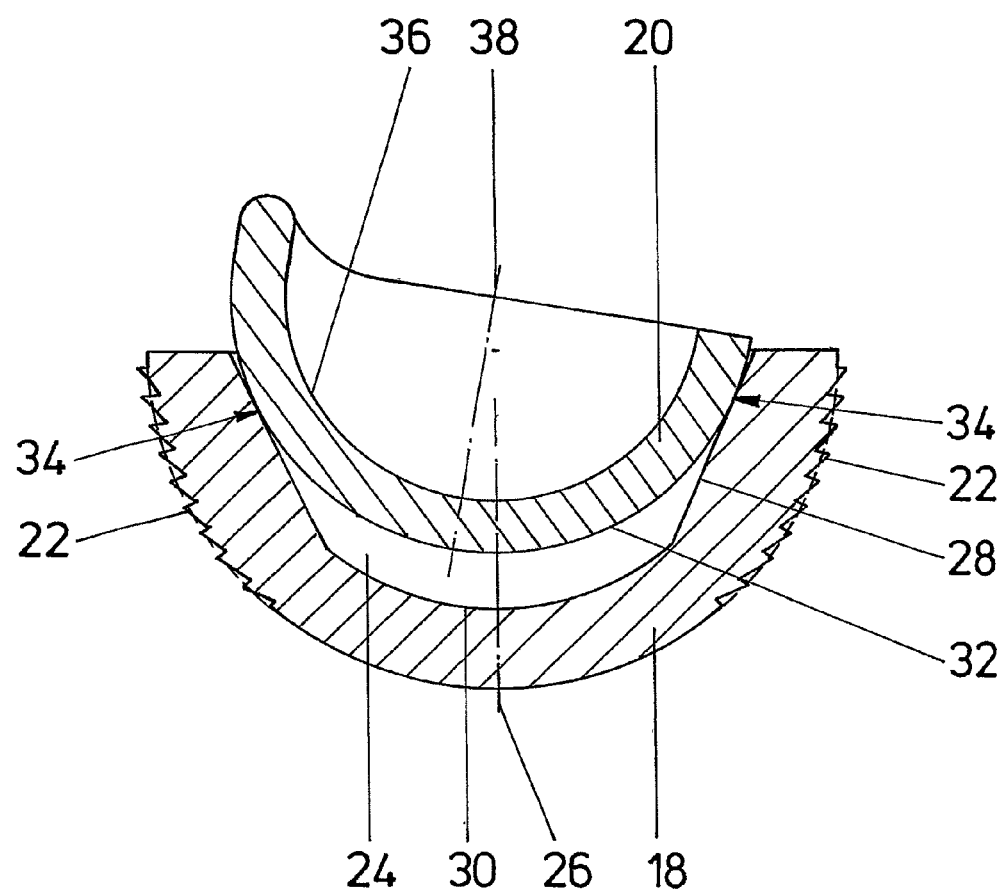
FIG. 2 is a schematic axial cross-section through the joint socket of the prosthesis in FIG. 1.

The joint socket separately shown in FIG. 2 consists of a socket shell 18 and a socket insert 20. The socket shell 18 is inserted in the pelvic bone 10 in a manner known per se. For that purpose, the socket shell 18 can be fixed in the pelvic bone 10 by means of additional screws. The socket shell 18 can be in the form of a screw socket, which has a thread on its outer surface, in the form of a press-in socket, which is formed having a suitable structure 22 on its outer surface, as shown by way of example in FIG. 2, or in the form of a re-operation socket, as is described, for example, in EP 0 663 193 A1.

The substantially hemispherical socket shell 18 is recessed by means of an accommodating space 24, which is open to the equatorial plane. The accommodating space 24 has rotational symmetry with respect to the mid-axis 26 of the socket shell 18. The accommodating space 24 has an internal surface 28 in the form of a straight circular cone (i.e., having an infinite radius of curvature) which becomes narrower from the opening located in the equatorial plane towards the pole of the socket shell 18. The base 30 of the accommodating space 24 in the pole region is flattened off. The cone angle of the conical inner surface 28, that is to say the angle included between the axis of rotation 26 and the lateral line of the inner surface 28, is so selected in dependence on the material pairing of socket shell 18 and socket insert 20 that self-retaining will come about. That angle is preferably about from 4° C. to 10° C. In the case of a metallic socket shell 18, for example, a self-retaining cone angle of about 4.5° C. is established for a metallic socket insert 20 and a self-retaining cone angle of about 9.5° C. for a ceramic socket insert 20.

The socket insert 20 is likewise of substantially hemispherical shape. The outer surface 32 of the socket insert 20 is spherically shaped at least in the region in which that outer surface 32 comes into contact with the inner surface 28 of the accommodating space 24. The diameter of the outer surface 32 corresponds to the diameter of the inner surface 28 at a line of contact 34, which extends, spaced somewhat (about from 5 mm to 15 mm) away from the equatorial opening plane, inside the accommodating space 24 concentrically with respect to the axis of rotation 26.

The socket insert 20 has a recessed spherical bearing surface 36, which serves to accommodate, and provide a bearing for, the joint head 16. The spherical outer surface 32 and the spherical bearing surface 36 are rotationally symmetrical with respect to an axis of rotation 38 of the socket insert 20.

The socket shell 18 is inserted in the pelvic bone 10, as shown in FIG. 1, the arrangement of the socket shell 18 in the pelvic bone 10 being selected in accordance with the anatomy and structure of the pelvic bone 10. The socket insert 20 is then loosely inserted in the accommodating space 24 of the socket shell 18. The outer surface 32 of the socket insert 20 comes into contact with the conical inner surface 28 of the accommodating space 24 along the line of contact 34. The socket insert 20 can then be rotated at will about its axis of rotation 38 and the axis of rotation 38 of the socket insert 20 can be tilted at will with respect to the axis of rotation 26 of the socket shell 18.

The prosthesis stem 12 is hammered into the cleared marrow cavity of the femur 40, the prosthesis stem 12 possibly adapting very slightly, in terms of its rotational position, to the bone structure of the femur. As a result, the position and orientation of the shaft neck 14 together with the joint head 16 become fixed in relation to the femur. The joint head 16 is then inserted into the bearing surface 36 of the socket insert 20, and the femur 40 together with the prosthesis stem 12 is brought into the optimum orthopaedic position. The socket insert 20 can then be oriented in accordance with that positioning. As soon as the socket insert 20 has been optimally oriented, the socket insert 20 is pressed axially into the accommodating space 24 so that it is clamped in self-retaining manner in that orientation position.

What is claimed is:

1. A joint socket for a hip endoprosthesis, comprising:
a socket shell configured to be implanted in the pelvic bone of a patient, the socket shell having an inner surface that defines an accommodating space extending about an axis of rotation; and
a socket insert configured to provide a bearing for a joint head of a prosthesis stem, a spherical outer surface of said socket insert configured to be disposed in the accommodating space of the socket shell and contact the inner surface of the socket shell along a line of contact that is concentric with the axis of rotation of the accommodating space of the socket shell, the line of contact being surrounded by and intersecting the spherical outer surface of the socket insert, the socket insert coupleable in a self-locking manner within said accommodating space along said line of contact,
wherein the inner surface of the socket shell tapers toward a pole of the shell in a region on either side of said line of contact in such a manner that a radius of curvature of the taper of the inner surface of the socket shell in the region of said line of contact is greater than the spherical radius of the outer surface of said socket insert at said line of contact when the shell and insert are in contact with each other.

2. The joint socket of claim 1, wherein the inner surface has a conical shape and defines an infinite radius of curvature in the region of said line of contact.

3. The joint socket of claim 2, wherein a cone angle of said conically shaped inner surface is a self-locking angle corresponding to a material pairing of said socket shell and said socket insert.

4. The joint socket of claim 3, wherein the cone angle of said conical inner surface is between about 4° and 10°.

5. The joint socket of claim 3, wherein the cone angle of said conical inner surface is about 4.5°.

6. The joint socket of claim 3, wherein the cone angle of said conical inner surface is about 9.5°.

7. The joint socket of claim 1, wherein the joint socket and the joint insert are configured to allow free rotation and tilting of the insert in the socket shell when the insert and shell are in contact with each other along said line of contact.

8. The joint socket of claim 1, wherein at least a portion of an outer surface of the socket shell comprises a threaded portion.

9. The joint socket of claim 1, wherein the socket shell is configured to be fixed in bone by one or more screws.

10. The joint socket of claim 1, wherein the accommodating space comprises a generally flat base.

11. The joint socket of claim 1, wherein the socket insert is a metallic socket insert.

12. The joint socket of claim 1, wherein the socket insert is a ceramic socket insert.

13. The joint socket of claim 1, wherein the line of contact is spaced between about 5 mm and 15 mm from an opening of the accommodating space.

14. The joint socket of claim 1, wherein said socket insert contacts said socket shell solely along said concentric line of contact.

15. The joint socket of claim 1, wherein the socket insert is monolithic.

16. A joint socket for a hip endoprosthesis, comprising:
a socket shell configured for implantation in a pelvic bone, the socket shell having an inner surface that defines an accommodating space extending about an axis of rotation; and
a socket insert comprising a bearing surface configured to receive a joint head of a prosthesis stem, the socket insert comprising a spherical outer surface configured for insertion in the accommodating space of the socket shell and configured to contact the inner surface of the socket shell along a line of contact that is concentric with the axis of rotation of the accommodating space, the socket insert coupleable in a self-locking manner within said accommodating space,
wherein the inner surface of the socket shell tapers toward a pole of the shell in a region on either side of said line of contact in such a manner that a radius of curvature in the region is greater than the spherical radius of the outer surface of said socket insert.

17. The joint socket of claim 16, wherein the line of contact intersects the spherical outer surface.

18. The joint socket of claim 16, wherein the inner surface has a conical shape and defines an infinite radius of curvature in the region axially surrounding said line of contact.

19. The joint socket of claim 18, wherein a cone angle of said conically shaped inner surface is a self-locking angle corresponding to a material pairing of said socket shell and said socket insert.

20. The joint socket of claim 19, wherein the cone angle of said conical inner surface is between about 4° and 10°.

21. The joint socket of claim 20, wherein the cone angle of said conical inner surface is about 4.5°.

22. The joint socket of claim 20, wherein the cone angle of said conical inner surface is about 9.5°.

23. The joint socket of claim 16, wherein said socket insert contacts said socket shell solely along said concentric line of contact.

24. The joint socket of claim 16, wherein the socket insert is monolithic.

25. A joint socket for a hip endoprosthesis, comprising:
a socket shell having an inner surface that defines an accommodating space extending about an axis of rotation, at least a portion of the accommodating space is in the form of a straight circular cone, the straight circular cone having a cone angle between about 4 degrees and 10 degrees; and
a socket insert having an outer surface, the outer surface is spherically shaped at least in a region in which the outer surface of the socket insert comes into contact with the inner surface of the straight circular cone when in use.

26. The joint socket of claim 25, wherein the socket shell and socket insert are coupleable in a self-locking manner along a contact between the spherically shaped region and the circular cone portion.

27. The joint socket of claim 25, wherein the socket shell and socket insert only contact between the spherically shaped region and the circular cone portion.

28. The joint socket of claim 25, wherein the socket insert is monolithic.

29. A joint socket for a hip endoprosthesis, comprising:
a socket shell having an inner surface comprising a tapered portion that extends about an axis of rotation and comprises a taper, the tapered portion at least partially defining an accommodating space configured to receive a socket insert;
a socket insert having an outer surface, the outer surface comprising a spherically shaped region having a radius of curvature, the socket insert being configured to contact the socket shell on the tapered portion along a line of contact concentric with the axis of rotation of the tapered portion when the socket insert is inserted into the accommodating space of the socket shell;
wherein a radius of curvature of the taper of the tapered portion surrounding the line of contact is greater than the radius of curvature of the spherically shaped region of the socket insert.

30. The joint socket of claim 29, wherein the tapered portion is conical.

* * * * *